United States Patent [19]

Koehler et al.

[11] Patent Number: 5,101,045
[45] Date of Patent: Mar. 31, 1992

[54] PREPARATION OF N-SUBSTITUTED PYRROLIDONES

[75] Inventors: Ulrich Koehler, Heidelberg; Hardo Siegel, Speyer, both of Fed. Rep. of Germany

[73] Assignee: BASF Aktiengesellschaft, Ludwigshafen, Fed. Rep. of Germany

[21] Appl. No.: 709,856

[22] Filed: Jun. 4, 1991

[30] Foreign Application Priority Data

Jun. 7, 1990 [DE] Fed. Rep. of Germany ....... 4018242

[51] Int. Cl.$^5$ .................. C07D 207/63; C07D 201/08
[52] U.S. Cl. .................... 548/554; 548/545; 548/552
[58] Field of Search ............................ 548/552, 554

[56] References Cited

U.S. PATENT DOCUMENTS

| | | | |
|---|---|---|---|
| 3,109,005 | 10/1963 | Lidov | 260/326.5 |
| 3,884,936 | 5/1975 | Hollstein | 260/326.5 |
| 4,814,464 | 3/1989 | Olsen | 548/552 |

FOREIGN PATENT DOCUMENTS 2321101 4/1973 Fed. Rep. of Germany .
3904083 11/1989 Fed. Rep. of Germany .

*Primary Examiner*—David B. Springer
*Attorney, Agent, or Firm*—Keil & Weinkauf

[57] ABSTRACT

A process for the preparation of N-substituted pyrrolidones by catalytic hydrogenation of maleic anhydride, maleic acid and/or fumaric acid in the presence of ammonia uses at least stoichiometric amounts of a primary alcohol or of an aldehyde and uses a catalyst which comprises cobalt and at least one of the elements manganese, copper, phosphorus, molybdenum and/or sodium.

10 Claims, No Drawings

PREPARATION OF N-SUBSTITUTED PYRROLIDONES

The present invention relates to a process for the preparation of N-substituted pyrrolidones by hydrogenating mixtures of maleic anhydride, maleic acid and/or fumaric acid in the presence of ammonia and at least stoichiometric amounts of an alcohol or aldehyde and in the presence of a catalyst which predominantly comprises cobalt and at least one of the elements manganese, copper, phosphorus, molybdenum and/or sodium.

The following abbreviations are used below: MAA for maleic anhydride, SAA for succinic anhydride, MA for maleic acid, FA for fumaric acid, SA for succinic acid and NMP for N-methylpyrrolidone.

U.S. Pat. No. 3,109,005 discloses the hydrogenation of mixtures of MAA and methylamine in the presence of Raney nickel to give N-methylpyrrolidone (NMP). At 270° C. and 250 bar, with dioxane as solvent and with reaction times of 10 hours, NMP yields of 70% are achieved by batch reactions in an autoclave.

Furthermore, DE-A-22 00 600 discloses the hydrogenation of MAA/methylamine mixtures in the presence of supported palladium catalysts to give NMP. The highest NMP yields achieved are 44%, at 275° C. and 120 bar in water as solvent. It is notable that virtually the same reaction conditions in the MAA/ammonia/water system give 2-pyrrolidone yields of up to 78%. NMP can accordingly be prepared in significantly lower yields than 2-pyrrolidone.

These moderate or unsatisfactory yields mean that these processes are not competitive with the conventional process for the preparation of NMP, i.e. the reaction of γ-butyrolactone with methylamine, and have thus achieved no industrial importance.

N-Substituted pyrrolidones, in particular NMP, are used and produced in large amounts as solvents and extractants. MAA is an inexpensive base chemical which is available in large amounts. It is therefore an object of the present invention to develop an economical process for the direct synthesis of N-substituted pyrrolidones by the catalytic hydrogenation of MAA/amine mixtures. In particular, it is an object to provide a catalyst which facilitates the preparation of said pyrrolidones in good yields and has a good service life.

We have found that this object is achieved by a process for the preparation of N-substituted pyrrolidones by the catalytic hydrogenation of maleic anhydride, maleic acid and/or fumaric acid in the presence of ammonia, which comprises using at least stoichiometric amounts of a primary alcohol or of an aldehyde and using a catalyst which comprises cobalt and at least one of the elements manganese, copper, phosphorus, molybdenum and/or sodium.

The process according to the invention is based on the hydrogenation of MAA(I)/ammonia mixtures to give N-substituted pyrrolidones (II) which can be described in formal terms by the reaction equation below:

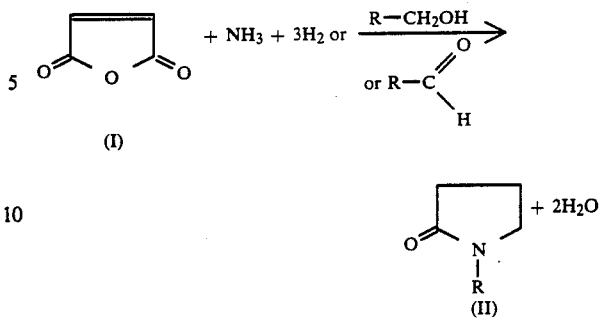

The use of as a starting material in the process according to the invention is equivalent to the use of MA and/or FA. All these starting materials can be introduced into the process according to the invention in solid, liquid or gaseous form. Particular preference is given to the use of MAA. Gaseous MAA, as generally formed on an industrial scale in the catalytic oxidation of butane, butene or aromatic hydrocarbons, is advantageously absorbed in a solvent, and the resultant solution is passed to the hydrogenation step without further work-up.

The novel catalytic hydrogenation of MAA/ammonia mixtures uses catalysts which comprise cobalt and at least one of the elements manganese, copper, phosphorus, molybdenum and/or sodium. Preferred catalysts comprise, in addition to cobalt, at least two of the elements manganese, copper, phosphorus, molybdenum and/or sodium. Particularly advantageous properties in the process according to the invention are exhibited by catalysts which, in addition to cobalt, comprise at least three of the elements manganese, copper, phosphorus, molybdenum and/or sodium. Catalysts of this type and their preparation are described in DE-A 23 21 101 and in DE-A-39 04 083 (corresponds to U.S. Pat. application Ser. No. 07/471 543).

Examples of catalysts which can advantageously be used in the process according to the invention are those whose catalytically active material comprises at least 40% by weight of cobalt (calculated as Co) and contains, as further active constituents, up to 10% by weight, preferably from 3 to 7% by weight, of manganese (calculated as Mn), up to 20% by weight, preferably from 0.1 to 5% by weight, of phosphoric acid and up to 1% by weight, preferably from 0.01 to 0.5% by weight, of sodium (calculated as Na). Particular preference is given to those of the abovementioned catalysts whose catalytically active material contains, as additional, catalytically active constituents, up to 30% by weight, preferably from 12 to 18% by weight, of copper (calculated as Cu) and up to 5% by weight, preferably from 1 to 4% by weight, of molybdenum (calculated as Mo).

The catalysts used according to the invention can be employed in the process according to the invention either as supported catalysts or preferably in compact form, i.e. without a carrier. The type of carrier material is generally unimportant; conventional carrier materials such as silica, alumina, titanium dioxides, activated charcoal, silicates or zeolites can be used. If necessary, binders or molding assistants can additionally be used to prepare the catalysts.

Before use in the process according to the invention, the catalysts are preferably activated using hydrogen.

This reduces the majority of the active catalyst constituents, which are generally in the form of their oxides after the calcination, generally giving the corresponding metals. Further details on the preparation of these catalysts can be obtained from DE-A 23 21 101 and DE-A-39 04 083.

In the process according to the invention, the catalysts can be used in suspended form, but a fixed-bed arrangement of the catalyst, through which the starting materials are passed in the pool or preferably trickle procedure, is preferred.

The hydrogenation according to the invention can be carried out in the presence of a solvent. Suitable solvents are aliphatic and cyclicethers, for example diethyl ether, methyl tert-butyl ether, dioxane or tetrahydrofuran, and/or the reaction products, for example N-methylpyrrolidone, particularly preferably water.

The molar MAA, MA or FA and ammonia to solvent ratio is from 1:0.001 to 1:100, in particular from 1:5 to 1:50. However, the reaction can also be carried out in the absence of solvents.

It is particularly advantageous to absorb in water the MAA, MA or FA from the gas mixtures produced on oxidation of n-butane or butenes and to use these solutions for the hydrogenation without further work-up.

The co-reactants used are primary alcohols, such as $C_1$- to $C_{12}$-alkanols, preferably $C_1$- to $C_4$-alkanols, for example methanol, ethanol, n-butanol, cyclohexanol, phenol or benzyl alcohol, or aldehydes, such as $C_1$- to $C_{12}$-aldehydes, for example formaldehyde, acetaldehyde or benzaldehyde.

The molar MAA, MA or FA to ammonia ratio is generally from 1:1 to 1:25, preferably from 1:1 to 1:5, particularly preferably from 1:1 to 1:3.

The molar ammonia to alcohol or aldehyde ratio is from 1:1 to 1:50, preferably from 1:1 to 1:20.

The hydrogenation is generally carried out at from 100° to 350° C., in particular at from 150° to 300° C., and at from 50 to 350 bar, in particular at from 100 to 300 bar.

In order to dissipate the high heat of hydrogenation without damaging the catalyst, it may be expedient to carry out the hydrogenation at two different temperature and/or pressure levels, with no work-up after the first temperature/pressure level. Thus, for example, the hydrogenation can be carried out first at from 100° to 220° C. and at from 50 to 200 bar and then completed at from 220° to 300° C. and at from 200 to 350 bar.

The hydrogenation can be carried out batchwise, but in particular continuously, in one or more reactors. The pool or, in particular, trickle procedure is used, with the catalyst in a fixed bed. However, it is also possible to employ a suspended catalyst. Both hydrogen and some of the hydrogenation product are recycled into the hydrogenation step.

Examples of reactors which can be used are tubular reactors or tube bundle reactors, it being possible to dissipate the heat of reaction by external cooling or, in the case of tubular reactors, by internal cooling. Examples of suitable reactor materials are standard stainless steels, for example RV steels.

In addition to the desired N-substituted pyrrolidones, the hydrogenation products may contain unsubstituted pyrrolidone and small amounts of (N-substituted)succinimides, succinic diamides, succinic monoamides and (N-substituted)pyrrolidines. Work-up may be by distillation and/or extraction. Intermediates which can be hydrogenated to give (N-substituted)pyrrolidones, such as, for example, the abovementioned (N-substituted)-succinimides and succinamides, can be separated off and recycled into the hydrogenation step.

EXAMPLES

EXAMPLE 1

Continuous hydrogenation of diammonium maleate/methanol

The hydrogenation was carried out in a tubular reactor (length 2 m, diameter 16 mm) which could be heated to the necessary temperature by means of oil via an external jacket. Gaseous and liquid feeds passed through the reactor together from top to bottom. The reactor discharge was cooled to room temperature and separated into liquid and gaseous streams. The catalyst used had the composition 66.8% by weight of CoO (=52.7% by weight of Co), 19.1% by weight of CuO (=15.3% by weight of Cu), 7.1% by weight of $Mn_2O_3$ (=5.1% by weight of Mn), 3.3% by weight of $MoO_3$ (=2.2% by weight of Mo), 3.5% by weight of $H_3PO_4$ (=1.1% by weight of P) and 0.15% by weight of $Na_2O$ (=0.1% by weight of Na). The catalyst was employed as 2.5–4.0 mm grit and activated with hydrogen before the hydrogenation was commenced.

At an overall pressure of 200 bar and a reactor internal temperature of 250° C., the hourly amounts indicated in Table 1 of diammonium maleate as a 45% strength solution in water, and methanol were fed into the reactor (circulation 9 l/h). Analysis of the liquid reactor product (distillation, GC) gave the following composition (Table 1, the data in mol % in each case relate to the diammonium maleate employed).

| Feed of diammonium maleate solution (ml/h) | Feed of methanol (ml/h) | Mol % | | | | |
|---|---|---|---|---|---|---|
| | | N-Methyl pyrrolidone | Succinimide methyl-succinimide | Pyrrolidone | Pyrrolidine methyl-pyrrolidine | Amides and salts of succinic acid |
| 90 | 45 | 43.4 | 5.7 | 41.6 | 3.1 | 2.2 |
| 90 | 90 | 80.3 | 4.9 | 5.8 | 2.9 | 2.1 |
| 135 | 135 | 60.5 | 11.2 | 18.7 | 1.0 | 5.3 |

EXAMPLE 2

Batchwise hydrogenation of diammonium maleate/methanol

In a 300 ml mini-autoclave, 75 ml of a 45% strength aqueous diammonium maleate solution and 75 ml of methanol were hydrogenated for 42 hours at 230° C. using 10 g of the powdered and activated catalyst described in Example 1. The product contained 89.1 mol % of N-methylpyrrolidone, 5.0 mol % of pyrrolidine and methylpyrrolidine, and 2.7 mol % of succinimide and methylsuccinimide.

EXAMPLE 3

Batchwise hydrogenation of diammonium maleate/formaldehyde

The procedure was similar to that described in Example 2, but the 75 ml of methanol were replaced by 150 ml of 35% strength formaldehyde solution. 65.3 mol % of N-methylpyrrolidone, 12.5 mol % of pyrrolidone, 6.1 mol % of pyrrolidine and methylpyrrolidine, and 15.1 mol % of succinimide and N-methylsuccinimide were obtained.

EXAMPLE 4

Continuous hydrogenation of diammonium maleate/butanol

A 2 m tubular reactor having a diameter of 41 mm was filled with the catalyst having the composition of Example 1 (pellets with a length of 7 mm and a diameter of 4 mm) and charged hourly at the reactor inlet with 500 ml of 45% strength aqueous diammonium maleate solution and 500 ml of n-butanol at a hydrogen pressure of 250 bar and a liquid circulation rate of 50 l/h.

The reactor products were worked up as described in Example 1. 57.3 mol % of N-butylpyrrolidone, 20.7 mol % of pyrrolidone, 5.7 mol % of pyrrolidine and butylpyrrolidine, 7.2 mol % of succinimide and butylsuccinimide, and 5.1 mol % of succinamides and salts were obtained.

We claim:

1. A process for the preparation of N-substituted pyrrolidones by catalytic hydrogenation of maleic anhydride, maleic acid and/or fumaric acid in the presence of ammonia, which comprises using at least stoichiometric amounts of a primary alcohol or of an aldehyde and using a catalyst which comprises cobalt and at least one of the elements manganese, copper, phosphorus, molybdenum and/or sodium.

2. A process as claimed in claim 1, wherein the primary alcohols used are $C_1$- to $C_{12}$-alkanols or the aldehydes used are $C_1$- to $C_{12}$-aldehydes.

3. A process as claimed in claim 1, wherein the active material of the catalyst comprises at least 40% by weight of cobalt.

4. A process as claimed in claim 1, wherein a catalyst is used whose active material comprises at least 40% by weight of cobalt and contains, as further active constituents, up to 10% by weight of manganese, up to 20% by weight of phosphoric acid and up to 1% by weight of sodium.

5. A process as claimed in claim 1, wherein a catalyst is used whose active material comprises at least 40% by weight of cobalt and contains, as further active constituents, up to 10% by weight of manganese, up to 30% by weight of copper, up to 5% by weight of molybdenum, up to 20% by weight of phosphoric acid and up to 1% by weight of sodium.

6. A process as claimed in claim 1, wherein a molar MAA, maleic acid and/or fumaric acid (including any secondary products present) to ammonia ratio of from 1:1 to 1:5, preferably from 1:1 to 1:3, is used.

7. A process as claimed in claim 1, wherein a molar ammonia to alcohol or aldehyde ratio of from 1:1 to 1:50, preferably from 1:1 to 1:20, is used.

8. A process as claimed in claim 1, wherein the alcohol used is methanol or the aldehyde used is formaldehyde.

9. A process as claimed in claim 1, wherein the hydrogenation is carried out at from 100° to 350° C., in particular at from 150° to 300° C., and at from 50 to 350 bar, in particular at from 100 to 300 bar.

10. A process as claimed in claim 1, wherein the hydrogenation is carried out at two different temperature and pressure levels, first at from 100° to 220° C. and at from 50 to 200 bar and subsequently completed at from 220° to 300° C. and at from 200 to 350 bar.

* * * * *